United States Patent

Maruzik et al.

Patent Number: 5,090,961
Date of Patent: Feb. 25, 1992

[54] SINGLE USE SYRINGE

[75] Inventors: Sergei M. Maruzik, Poltava; Oleg V. Efremov, Karlovka, both of U.S.S.R.

[73] Assignee: Poltavsky Meditsinsky Stomatologyichesky Institut, Poltava, U.S.S.R.

[21] Appl. No.: 623,724
[22] PCT Filed: Oct. 4, 1989
[86] PCT No.: PCT/SU89/00261
§ 371 Date: Dec. 21, 1990
§ 102(e) Date: Dec. 21, 1990
[87] PCT Pub. No.: WO90/12612
PCT Pub. Date: Nov. 1, 1990

[30] Foreign Application Priority Data

Apr. 24, 1989 [SU] U.S.S.R. ............... 4682845

[51] Int. Cl.$^5$ ............. A61M 5/00; A61M 5/315
[52] U.S. Cl. ................... 604/110; 604/222; 604/228
[58] Field of Search ............. 604/110, 218, 221, 222, 604/228

[56] References Cited

U.S. PATENT DOCUMENTS 4,233,975 11/1980 Yerman .
4,687,467 8/1987 Cygielski .
4,775,363 10/1988 Sandsdalen .
4,923,443 5/1990 Greenwood et al. ............... 604/110
4,973,308 11/1990 Borras et al. ...................... 604/110

FOREIGN PATENT DOCUMENTS 0282097 9/1988 European Pat. Off. .
0325886 8/1989 European Pat. Off. ........... 604/110
0340899 11/1989 European Pat. Off. ........... 604/110
8909074 10/1989 PCT Int'l Appl. ................. 604/110

Primary Examiner—John D. Yasko
Assistant Examiner—Sharon Finkel
Attorney, Agent, or Firm—Fleit, Jacobson, Cohn, Price, Holman & Stern

[57] ABSTRACT

A disposable syringe for injections has a cylindrical housing (1), which accommodates a piston (2) with a rod (3) and a needle fixing device. The piston (2) and the rod (3) are mechanically disengaged from each other and the rod (3) has an annular two-stepped slot (5), wherein provision is made for a lower-depth portion (6) and a higher-depth portion (7). A sealing cup (8) made of an elastic material is interference-fitted in the portion (6) of the slot (5), the width of the cup (8) being in excess of the clearance (b) between the bottom of the slot (5) in the portion (6) thereof and the inner surface of the housing (1).

2 Claims, 3 Drawing Sheets

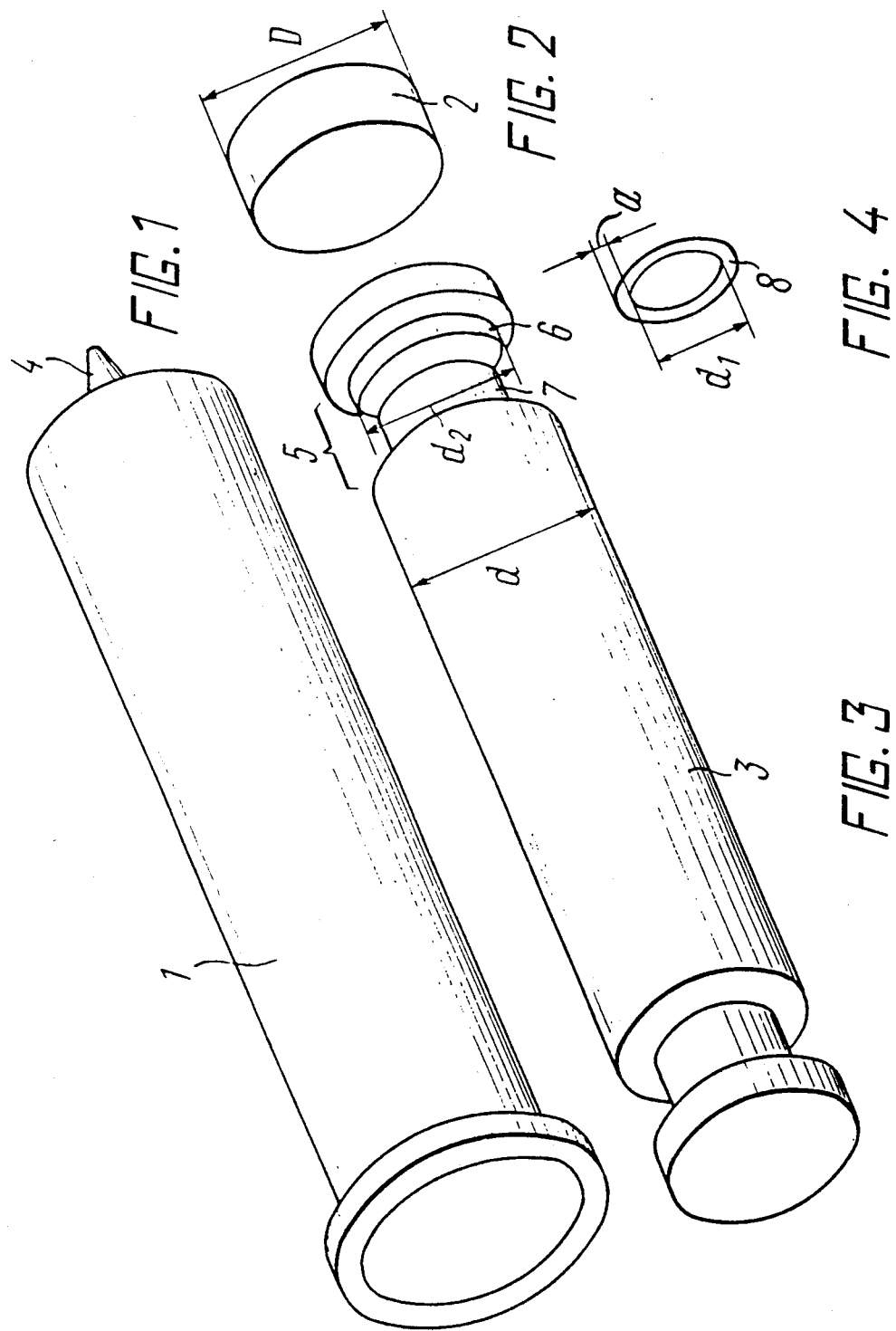

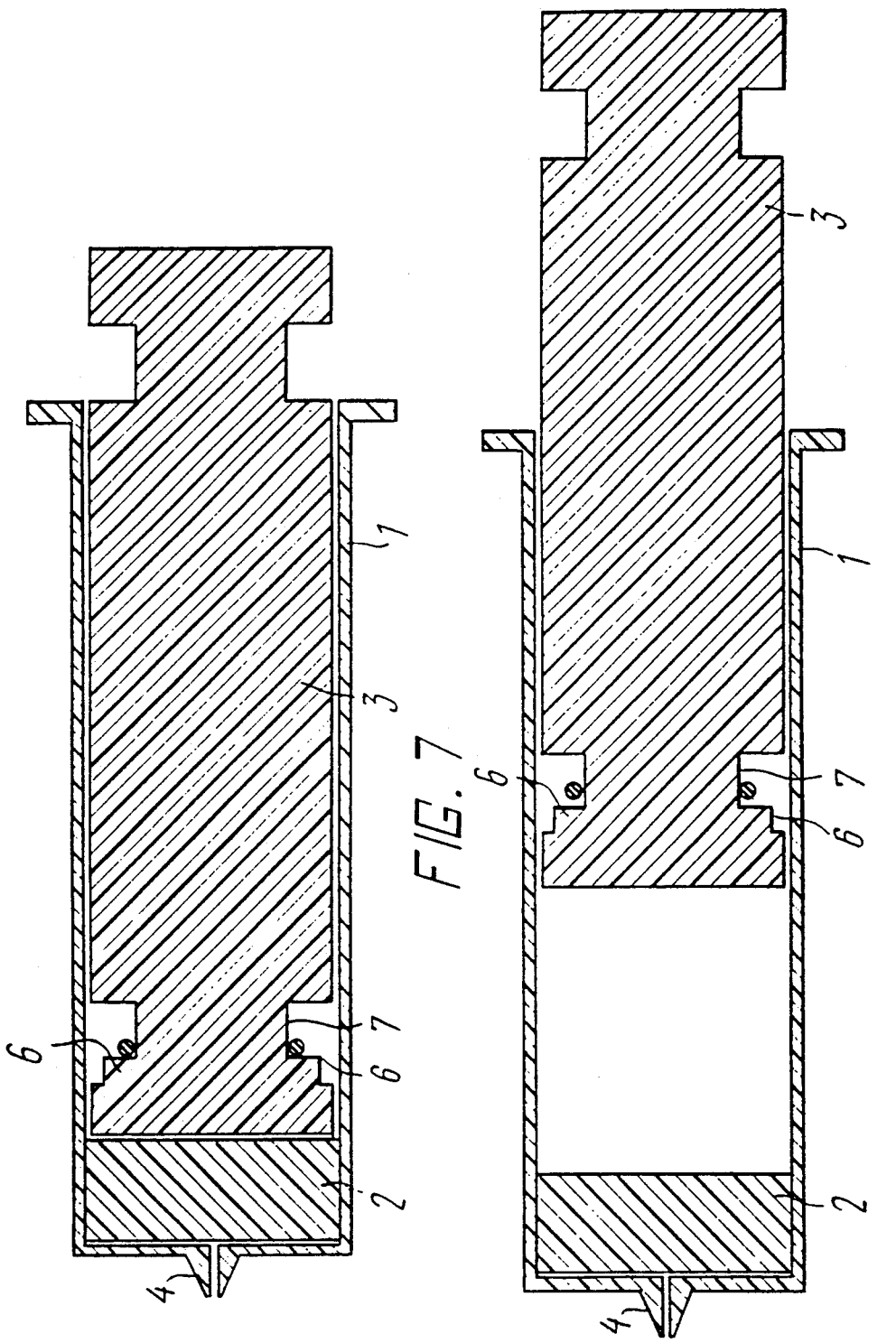

5,090,961

SINGLE USE SYRINGE

TECHNICAL FIELD

This invention relates generally to medical engineering and, more specifically, to disposable syringes applied for injections.

PRIOR ART

Some disposable syringes for injections known to be in widespread use nowdays comprise a cylindrical housing, a piston with a rod accommodated in said housing, and a needle fixing device (cf., e.g., disposable syringes available from Trumo Europe Co., Belgium). The syringes in question differ practically in nothing from disposable syringes now in extensive use in modern medical practice, the sole exception residing in that they are made of a cheaper material (i.e., polymer) and therefore are not subject to sterilization. This means that the construction of the known disposable syringes enables one to make repeated use of them, which may occur on account of inattention or unscrupulousness on the part of medical staff, or when injections are made by those who are in narcotic or alcoholic intoxication. All stated above proves to be of importance, since such cases are fraught with a danger of infection with the virus of AIDS, that of infections hepatitis, and of some other diseases.

One more prior-art disposable syringe is known to comprise a cylindrical housing accommodating a piston with a rod, and a needle fixing device (EP, A, 0282097).

The syringe under discussion features its needle fixed in a washer situated in the front portion of the syringe housing and capable of reciprocating lengthwise the axis of the housing. The piston disposed past the washer in the syringe housing and rigidly coupled to the rod is not engaged with the washer but has catches adapted for the piston to engage the washer when both of them interact with each other through their end faces. At the end of the injection when the piston and the washer get in contact with each other through their end faces, the piston becomes engaged rigidly, by means of the catches, with the washer, wherein the needle is fixed, with the result that any attempt to repeatedly draw a fresh portion of injectant substance in the syringe, the washer together with the needle is entrained by the piston into the housing of the syringe. As soon as the needle gets inside the housing it is offset with respect to the axis of the housing so that any attempt to perform an injection results in breakade of the injection needle.

However, the aforedescribed construction leaves room for reusing a syringe, since the piston gets engaged with the washer only when in its fully advanced position in the front portion of the housing. This causes the needle to be retracted into the housing, whereby the syringe gets unfit for further use. Should the piston be not brought to the fully advanced position during injection, the syringe can be applied for making an unlimited number of injections involving almost complete utilization of the holding capacity of its housing.

DISCLOSURE OF THE INVENTION

It is a primary and essential object of the invention to develop such a construction of a disposable syringe for injections that would prevent any possibility of reusing such a syringe.

The essence of the invention resides in the fact that in a disposable syringe for injections, comprising a cylindrical housing, which accommodates a piston with a rod and a needle fixing device, according to the invention, the piston and the rod are mechanically disengaged from each other, the diameter of the rod is less than the piston diameter and the rod is provided with an annular two-stepped slot, wherein its lower-depth portion is situated closer to the rod end facing the piston, a sealing cup made of an elastic material is located in said slot portion, the inside diameter of said cup being lesser that the rod diameter at the place where said lower-depth slot portion is situated, while the depth of said cup exceeds a clearance between the slot bottom in its lower-depth portion and the inner surface of the housing.

It is expedient that the rod diameter 'd' be so selected as to satisfy the ratio $d/D = 0.9$, where D stands for the rod diameter.

The disposable syringe for injection, according to the present invention, makes imposaible repeated injections, is simple to manufacture, and reliable in operation. Production costs of such a disposable syringe, according to the invention, do not practically exceed those of the heretoforeknown disposable, syringes.

SUMMARY OF THE DRAWINGS

In what follows the invention will now be disclosed in a detailed description of a specific exemplary embodiment thereof given by way of illustration with reference to the accompanying drawings, wherein:

FIGS. 1, 2, 3, 4 present a perspective disassembled view of a disposable syringe for injections, according to the invention;

FIG. 6 is a view of the disposable syringe of FIG. 5 at the instant when an injection substance is drawn in;

FIG. 7 is a view of the disposable syringe of FIG. 5 as shown after injection; and FIG. 8 is a view of the disposable syringe of FIG. 5 while an attempt is made to repeatedly draw in an injection substance.

PREFERRED EMBODIMENT OF THE INVENTION

Figure 5:
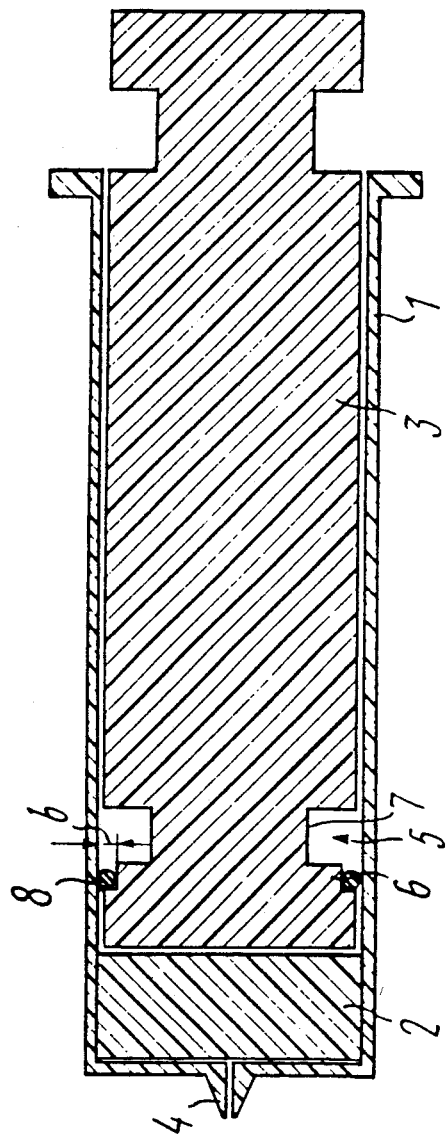
FIG. 5 is a longitudinal sectional view of a disposable syringe for injections, according to the invention, while in the initial position.

The disposable syringe for injections, according to the invention, comprises a cylindrical housing 1 (FIGS. 1, 5), which accommodates a piston 2 (FIGS. 2, 5) with a rod 3 (FIGS. 3, 5). The housing 1 is provided with a device for fixing the needle (omitted in the Drawing), i.e., a cannula 4 (FIGS. 1, 5) situated at the front end face of the housing 1. The piston 2 and the rod 3 are mechanically disengaged from each other, while the diameter 'd' of the rod 3 (FIG. 3) is smaller than the diameter 'D' of the piston 2 (FIG. 2). It is desirable that the ratio d/D be approximately 0.9. The rod 3 (FIG. 1) is provided with a two-stepped annular slot 5, which has a lower-depth portion 6 and a higherdepth portion 7, the portion 6 being located closer to that end of the rod 3 (FIG. 5 which faces towards the piston 2. A sealing cup 8 (FIGS. 4, 5) is interference-fitted onto the portion 6 of the piston 3, said cup 8 being made of an elastic material, such as rubber. The inside diameter $d_1$ of the diameter $d_1$ of the cup 8 is smaller than the diameter $d_2$ of the portion 6 of the rod 3, while the width 'a' of the cup 8 exceeds the clearance 'b' between the bottom of the portion 6 of the slot 5 and the inner surface of the wall of the housing 1. The cup 8 establishes hermetic sealing of the space confined within the piston 2 and the rod 3.

The application technique of the disposable syringe for injections proposed herein is as follows.

Figure 6:
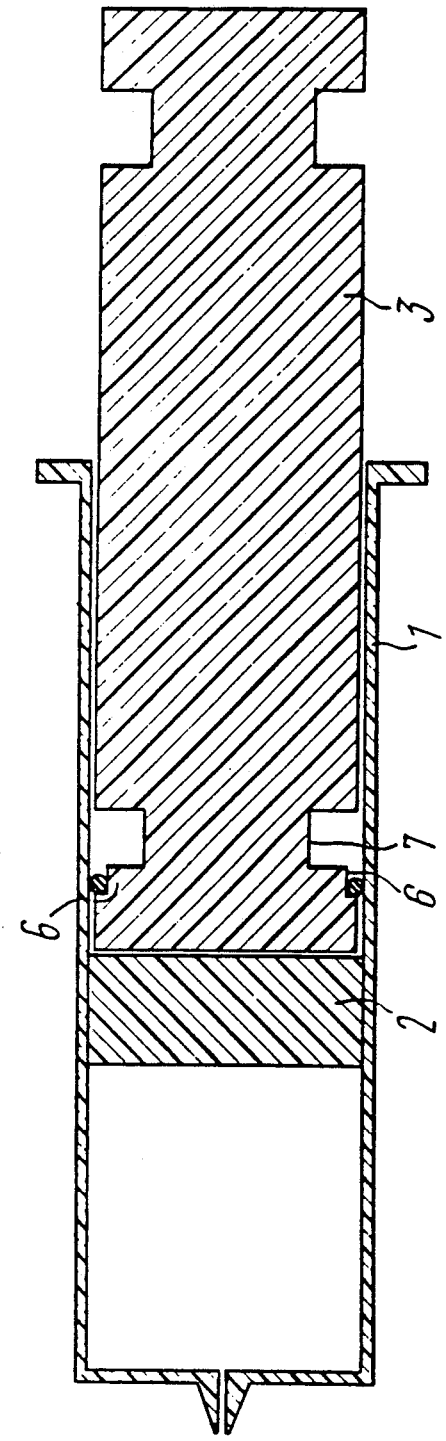

When in the initial position the rod 3 (FIG. 5) is retracted into the housing 1 of the syringe, while the piston 2 is situated at the front end face of the housing 1 carrying the needle-mounting cannula 4. The rod 3 is arranged close to the piston 2, while the cup 8 is located in the portion 6 of the slot 5. Upon advancing the rod 3 (FIG. 6) from the housing 1 the cup 8 gets tightly pressed against the inner surface of the housing 1 and rests against the projection provided in the portion 6 of the rod 3 of the syringe. As a result, a negative pressure is established in between the rod 3 and the piston 2, whereby the latter is made to travel after the rod 3 throughout its pathway. Thus, an injection substance is drawn in the space of the housing 1 before the rod 3. To perform injection the rod 3 is to be retracted into the housing 1, with the result that the cup 8 is free to move, due to elastic forces developed by the material said cup is made of, as well as by virtue of a difference between the diameters $d_1$ and $d_2$, along the slot 5 from its larger-diameter portion 6 to the smaller-diameter portion 7. As a result, hermetic sealing of the space confined between the piston 2 and the rod 3 is disturbed so that the piston can no longer travel after the rod 3 upon drawing in a fresh portion of the injection substance, that is, the syringe becomes unfit for further use after a single injection made with the aid of it, since retraction of the piston 2 is impossible inasmuch as it occurs by virtue of rarefaction, which cannot be established without fitting the cup 8 in the portion 6 of the slot 5 (FIG. 5).

The fact that the ratio $d/D$ is approximately 0.9 hampers access to the cup 8 and makes it impossible to bring the syringe to the initial (working) state under nonindustrial conditions.

Widespread application of the proposed syringe will help practically rule out patient's infection, during injections, with the virus of AIDS, that of infections hepatitis, and of some other diseases communicable by parenteral administration of medical agents.

INDUSTRIAL APPLICABILITY

The syringe is aimed at widespread application in medical institutions and for individual use.

What is claimed is:

1. A disposable syringe comprising a cylindrical housing (1), which accommodates a piston (2) with a rod (3), and a needle fixing device, characterized in that the piston (2) and the rod (3) are mechanically disengaged from each other, the diameter (d) of the rod (3) is smaller than the diameter (D) of the piston (2), and the rod (3) has an annular two-stepped slot (5) with a lower-depth portion (6) and an increased-depth portion (7), wherein its lower-depth portion (6) is situated closer to one end of the rod (3) which faces the piston (2) than is the increased-depth portion, and an annular sealing cup (8) made of an elastic material situated on the lower-depth portion (6) of the slot (5), the inside diameter ($d_1$) of said cup (8) being smaller than the diameter ($d_2$) of the lower-depth portion (6) of the slot (5), while the radial width (a) of the cup exceeds a clearance (b) between the lower-depth portion (6) and the inner surface of the housing (1), the cup providing a hermetic seal between the rod and the piston for initial use of the rod in unison to draw fluid into the housing, the cup being movable from the lower-depth portion of the slot into the increased depth portion of the slot when the rod is used to discharge the fluid from the housing thereby breaking the hermetic seal and preventing further use of the syringe.

2. A disposable syringe for injections as claimed in claim 1, characterized in that the diameter 'd' of the rod (3) is about 0.9, times the diameter of the piston (2).

* * * * *

UNITED STATES PATENT AND TRADEMARK OFFICE
CERTIFICATE OF CORRECTION

PATENT NO. : 5,090,961
DATED : February 25, 1992
INVENTOR(S) : Sergei Mikhailovich MAZURIK et al.

It is certified that error appears in the above-identified patent and that said Letters Patent is hereby corrected as shown below:

On the Title page, the correct spelling of the first inventor's name is --Mazurik--.

Signed and Sealed this

Eighth Day of June, 1993

Attest:

MICHAEL K. KIRK

*Attesting Officer*          *Acting Commissioner of Patents and Trademarks*